(12) United States Patent
Camenisch

(10) Patent No.: US 6,938,504 B2
(45) Date of Patent: Sep. 6, 2005

(54) METHOD AND DEVICE FOR EVALUATING A LIQUID DOSING PROCESS

(75) Inventor: Johann L. Camenisch, Chur (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 10/471,242

(22) PCT Filed: Mar. 7, 2002

(86) PCT No.: PCT/EP02/02521

§ 371 (c)(1),
(2), (4) Date: Sep. 9, 2003

(87) PCT Pub. No.: WO02/073215

PCT Pub. Date: Sep. 19, 2002

(65) Prior Publication Data

US 2004/0089051 A1 May 13, 2004

(30) Foreign Application Priority Data

Mar. 9, 2001 (DE) .......................................... 101 11 423
Oct. 2, 2001 (DE) .......................................... 101 48 608

(51) Int. Cl.⁷ .............................. B01L 3/02; G01M 3/02; G01F 19/00
(52) U.S. Cl. .......................... 73/864.01; 73/37; 73/1.74
(58) Field of Search .............................. 73/1.05, 23.21, 73/1.34, 1.59, 1.61, 1.68, 1.74, 41.3, 41.4, 863.32, 864.14, 864.16, 863.01, 436, 864.01; 702/82, 83, 84, 113

(56) References Cited

U.S. PATENT DOCUMENTS

| 4,448,058 A | * | 5/1984 | Jaffe et al. ..................... 73/23.3 |
| 4,715,214 A | * | 12/1987 | Tveter et al. .................. 73/49.2 |
| 4,743,228 A | * | 5/1988 | Butterfield ................... 604/505 |
| 5,182,938 A | * | 2/1993 | Merkel ....................... 73/19.05 |
| 5,463,895 A | * | 11/1995 | Brentz ........................ 73/61.71 |
| 5,488,854 A | * | 2/1996 | Kawanabe et al. ........ 73/19.05 |
| 5,488,874 A | * | 2/1996 | Kawanabe et al. ...... 73/863.01 |
| 5,503,036 A | * | 4/1996 | Nguyen et al. .......... 73/864.34 |
| 5,537,880 A | * | 7/1996 | Takeda et al. ........... 73/864.25 |
| 5,540,081 A | * | 7/1996 | Takeda et al. .................. 73/37 |
| 5,992,229 A | * | 11/1999 | Pyotsia et al. ................ 73/168 |
| 6,094,966 A | * | 8/2000 | Papen et al. .................. 73/1.74 |
| 6,121,049 A | * | 9/2000 | Dorenkott et al. ............ 436/50 |
| 6,370,942 B1 | * | 4/2002 | Dunfee et al. .................. 73/37 |
| 2002/0052702 A1 | * | 5/2002 | Keller ......................... 702/84 |

FOREIGN PATENT DOCUMENTS

| EP | 0 982 593 A | 3/2000 |
| EP | 0 990 909 A | 4/2000 |
| EP | 1 048 953 A | 11/2000 |
| WO | WO 92/08545 A | 5/1992 |
| WO | WO 98/53325 A | 11/1998 |
| WO | WO 01/88549 A | 11/2001 |

OTHER PUBLICATIONS

J.P. Holman, Experimental Methods for Engineers, 5ᵗʰ Edition, McGraw–Hill, Inc., pp. 37–84.*

* cited by examiner

Primary Examiner—Hezron Williams
Assistant Examiner—John Fitzgerald
(74) Attorney, Agent, or Firm—Rothwell, Figg, Ernst & Manbeck

(57) ABSTRACT

The invention relates to a method for evaluating a liquid dosing process in a container which is at least partially filled with a gas. According to the inventive method, a temporal course of at least one state variable p of a medium contained in said container is determined essentially over the entire duration of the dosing process. The temporal course (40; 40') of the at least one state variable (p) is graphically or mathematically compared with a pre-determined state variable nominal range (42; 42'; 242) by means of a correlation method, and an evaluation result (S6, S14, S16) is obtained according to the results of the comparison.

21 Claims, 5 Drawing Sheets

METHOD AND DEVICE FOR EVALUATING A LIQUID DOSING PROCESS

CROSS REFERENCE TO RELATED APPLICATION

Figure 1:
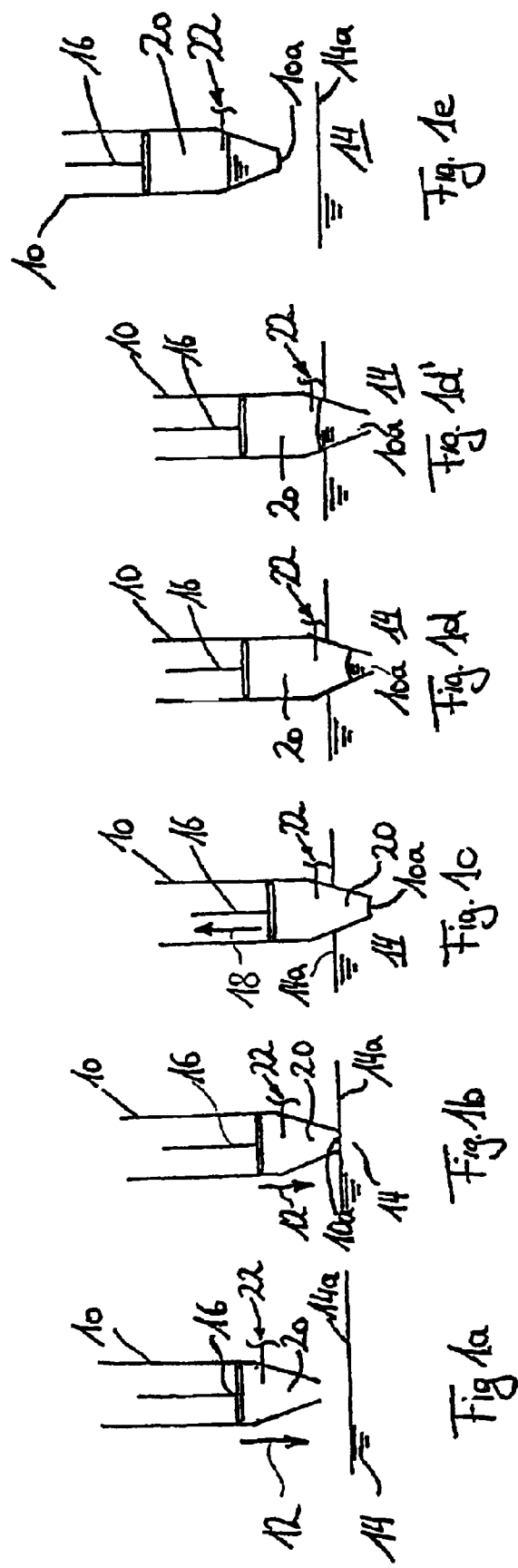

This application is a 35 USC § 371 National Phase Entry Application from PCT/EP02/02521, filed Mar. 7, 2002, and designating the U.S.

DESCRIPTION

The present invention relates to a method and a device for evaluating a liquid dosing process in a container which is at least partially filled with a gas.

Liquid dosing processes are often part of mixing or analyzing procedures in which exact doses of liquids are taken from liquid quantities and mixed together, for example. Liquid dosing processes are routine in chemical, pharmaceutical, medical and human biological processes. Many of these dosing processes are part of a manufacturing process for production of pharmaceutical or medical active ingredients and drugs or they make a contribution toward making a medical diagnosis of diseases. Undetected faulty liquid dosing can therefore result in products which are objectionable or even harmful for the health of living creatures, in particular humans. However, even if faulty liquid dosing is detected in an operational or clinical quality assurance stage, there is still the risk of wasting valuable substances, which under some circumstances are available only in limited amounts due to an unnecessarily large number of reject doses.

Therefore, it is extremely important to be able to evaluate liquid dosing processes as soon as possible with the greatest possible certainty as to whether the process is fault-free.

Various methods are known from the state of the art for evaluating a liquid doing process, e.g., for an aspiration process, i.e., intake of a liquid and for a dispensing process, i.e., dispensing a liquid in pipetting.

In an aspiration process, the tip of the pipette is first immersed in the liquid to be taken up. Therefore, a quantity of gas present in a liquid holding space bordered by the pipette tip opening, the pipette tip inside wall and the plunger is sealed off and separated from the gas volume of the environment so that the quantity of gas present in the pipette tip remains approximately constant, i.e., apart from evaporation and condensation processes. Due to an intake movement of the pipetting plunger away from the pipette tip, the volume of the quantity of gas that is sealed off is increased, so that the pressure of the gas in the liquid holding space drops. Beyond a certain pressure difference between the gas pressure in the liquid holding space and the ambient gas pressure, liquid begins to flow through the pipette tip opening into the liquid holding space. Due to the liquid flowing in, the rate of change in gas volume declines and thus the rate of change in gas pressure in the liquid holding space also drops.

In the known methods of evaluating a liquid dosing process, monitoring is provided to ascertain whether the gas pressure in the liquid holding space drops below a predetermined limit value. In some processes, the rate of change in the pressure of the gas enclosed in the liquid holding space is also observed in addition to whether the prevailing value drops below a limit value, i.e., a check is performed to determine whether the gas pressure in the liquid holding space changes by a predetermined amount in a predetermined period of time. This check can be performed graphically by comparing the slope of a pressure-time curve with a predetermined slope or analytically by comparing corresponding pressure-time value pairs.

For the dispensing process in which the volume of a quantity of gas enclosed between a liquid that has been taken up and the pipetting plunger is to be reduced by a displacement movement of the pipetting plunger toward the pipette opening, the evaluation process described previously is also applicable accordingly. It is true in general that the dosing process is evaluated as fault-free if the pressure of the gas enclosed in the liquid holding space has reached, exceeded or fallen below a certain limit value and/or if the change in pressure over time reaches, exceeds or falls below a certain limit value.

One disadvantage of this state-of-the-art method is that the evaluation as to whether or not the liquid dosing process has taken place without any errors is based on only a few measured values, which are usually measured at the beginning of the dosing process. An error which occurs after reaching the gas pressure limit value is no longer detected by this method. Such an error may occur, for example, when the pipette tip opening is clogged due to a solid present in the liquid during the inflow of liquid into the pipette tip. This may be the case when dosing blood, for example, if coagulated components are present in the liquid blood.

Therefore, the object of the present invention is to provide a teaching which will make it possible for those skilled in the art to reliably evaluate liquid dosing processes with regard to their successful completion and to promptly detect faulty dosing.

According to a first aspect of the present invention, this object is achieved by a method of evaluating a liquid dosing process in a container which is filled at least partially with a gas, preferably with air, in particular an aspiration and/or dispensing process in pipetting, in which process a time characteristic of at least one state variable of a medium that is present in the container is detected essentially over the entire duration of the dosing process, in which moreover essentially the entire chronological course of the at least one state variable is compared with a predetermined state variable setpoint range, and in which an evaluation result is output dependent on the result of the comparison.

Although in the acknowledgment of the state of the art, a process for evaluating a pipetting procedure has been described, the inventive method is not limited to pipettes as containers, but instead may be applied to any containers. Due to the fact that at least one state variable of a medium present in the container is detected over essentially the entire duration of the dosing process, information is available regarding the filling level of the container essentially for the entire dosing process and can be used to evaluate it. By comparing essentially the entire chronological course of the at least one state variable with a state variable setpoint range, abnormal values of the at least one state variable occurring at any point in time during the dosing can be detected, and thus the dosing process can be evaluated reliably.

The state variable setpoint range may be, for example, an idealized state variable characteristic which is provided with an additional tolerance allowance under some circumstances.

The state variable can be detected in any medium present in the container. For example, the state variable may be the hydrostatic pressure of the liquid dosed into an open beaker or a bottle, this pressure being measured at the lowest point in the beaker or bottle. Frequently, however, containers having a gas space sealed off during the dosing process are used for liquid dosing, as is the case, for example, in pipetting with pipette tips. In such containers, by detecting at least one state variable of the gas present in the container, it is possible to obtain a particularly accurate result because in contrast with the liquid flowing in or out, the quantity of gas enclosed in the container is influenced almost exclusively by the liquid to be dosed, and any influence by the environment of the container is virtually ruled out.

Another advantage of detecting at least one state variable of the gas present in the container is that in this way it is also possible to evaluate dosing processes using smaller dosing quantities than in the case of determination of a state variable of the dosed liquid itself, because the liquid is subject to adhesion interactions and/or frictional interactions with the wall of the container to an even greater extent than is the gas. These interactions become negligible only beyond a certain minimum quantity of liquid.

The inventive method can be implemented with any type of gas, i.e., in any type of gas atmosphere. In the simplest and most common case, the dosing process is carried out in ambient air, which is why the containers in this case are filled with air. However, it is also conceivable for liquids whose contact with air or oxygen is not desirable to be dosed. In this case, the inventive method may also be used in dosing in an inert or quasi-inert atmosphere such as an argon, nitrogen or carbon dioxide atmosphere.

As described above, the hydrostatic pressure may be used as the state variable for a measurement in a liquid present in the container and the gas pressure and/or temperature may be used for a measurement in the gas. Since the quantity of gas present in the container, i.e., the gas mass, remains approximately constant during the dosing process in many dosing containers, but the volume of the quantity of gas is altered due to movement of a plunger, therefore the pressure changes with the volume and, depending on the execution of the dosing process, the temperature of the gas also changes. In the case of especially slow changes in gas volume in the container, it is possible to approximately assume an isothermal change in volume. In this case, only measurement of the pressure has any relevance. When there are particularly rapid changes in volume, it is possible in first approximation to assume an adiabatic change in state, which is why with a knowledge of the adiabatic exponent assigned to the gas, either the pressure or the temperature can be determined as additional state variables. The greatest accuracy and reliability, however, are obtained by detecting both the pressure and temperature of the gas because then there can be mutual monitoring of the functional reliability of the state variable detection sensors.

For determination of a state variable, it is sufficient to determine a variable which changes in a known relationship to the state variable.

The state variable setpoint range is advantageously defined at least for the entire duration of the liquid dosing process. In this case, it is possible to evaluate the liquid dosing process not only in certain intervals of time but in fact at any point in time during the dosing process.

However, this does not mean that the state variable setpoint range is defined only for the duration of the change in the quantity of liquid in the container. It may also be appropriate to also determine the state variable before and/or after the phase of the change in the quantity of liquid in the container and also to extend the state variable setpoint range to these intervals of time accordingly. Thus, a transport phase, if any, between the aspiration phase and the dispensation phase can be monitored, e.g., for loss of liquid due to formation of droplets and loss of droplets or even loss of the pipette tip.

The precise procedure for determining such processes before and after the liquid dosing is described further below on the basis of one exemplary embodiment.

According to a first preferred embodiment of the present invention, the state variable setpoint range may be defined as following a setpoint curve, in which case then to evaluate the dosing process it is determined whether the time characteristic of the at least one state variable is within the state variable setpoint range and an evaluation result is output dependent on of the result of the determination. This is a comparison which is very simple to perform and with which a dosing process can be evaluated reliably.

For reasons of the greatest possible clarify and ease of understanding of the evaluation results obtained, the state variable setpoint range may advantageously be defined in such a way that the liquid dosing process is evaluated as error-free as long as the time characteristic detected for the at least one state variable is within the state variable range, and it is evaluated as faulty if it is found that the time characteristic determined for the at least one state variable is outside of the state variable setpoint range in at least some segments.

For example, a pipette opening may be clogged temporarily by a solid or its cross section may be reduced, and after a period of delay, the solid is rinsed away by the liquid flowing in or out. In this case, the gas pressure in the interior of the pipette tip would drop sharply, e.g., in an aspiration process (and/or the gas temperature would drop sharply), so that the state variable would leave its setpoint range. After eliminating the problem, the state variable may again assume values within the setpoint range. However, since undefined flow conditions prevailed at the pipette tip while the problem was occurring, it is advisable to evaluate a pipetting process as faulty if it is found that the time characteristic determined for the at least one state variable is outside of the state variable setpoint range in at least some segments.

Another advantage of the inventive method is the possibility of diagnosing an error if it occurs to determine the type of error in addition to evaluating a correct sequence of the dosing process. To do so it is advantageous that when the time characteristic of the at least one state variable is determined as being outside of the state variable setpoint range in at least some segments, it is determined whether in at least some segments the characteristic of the at least one state variable is in at least one error range of a plurality of error ranges of a state variable value range which is outside of the state variable setpoint range. Then an error message is output dependent on at least one error range that has been passed through.

If the time characteristic of the at least one state variable leaves the state variable setpoint range, then the time characteristic of the at least one state variable is in a state variable value range which is outside of the state variable setpoint range. Then different types of errors usually occur at different times and/or lead to different deviations in the state variable value from the state variable setpoint range. It is therefore possible to subdivide the state variable value range surrounding the state variable setpoint range into at least one error range, preferably a plurality of error ranges. Each error range is advantageously assigned precisely one error, or under some circumstances it may also be assigned a plurality of errors. In the case of a plurality of error ranges, they are differentiated from one another in time and/or through state variable threshold values, optionally variable over time.

Likewise, the state variable setpoint range may be delimited by an upper and a lower threshold curve from the remaining state variable value range. The upper threshold curve is the threshold curve which limits the state variable setpoint range toward higher state variable values. The lower threshold curve is accordingly the threshold curve which limits the state variable setpoint range toward lower state variable values. The threshold curves may be functions of time and in fact they usually are because the state variable setpoint range usually follows a nontrivial setpoint curve. In this case, the determination of whether the time characteristic of the at least one state variable is within the predetermined state variable setpoint range can be performed easily by a comparison of the time characteristic with the upper threshold curve and the lower threshold curve.

As an alternative to this, the determination of whether the time characteristic of the at least one state variable is within the predetermined state variable setpoint range may also be performed by image processing. An image processing determination method is facilitated by the inventive method inasmuch as the databases used in the process, e.g., the time characteristic of at least one state variable, state variable setpoint range and, if desired, a plurality of error ranges are especially suitable for a graphic representation and analysis.

The quality of the evaluation of the liquid dosing process achieved with the inventive method depends to a great extent on the state variable setpoint range used for the evaluation. If the state variable setpoint range has been chosen to be very broad, there is the risk that dosing processes that are already faulty might be evaluated as fault-free. Conversely, if the state variable setpoint range is chosen to be very narrow, this entails the risk that fault-free dosing processes might be evaluated as faulty.

A state variable setpoint range of a certain liquid dosing process which is particularly suitable for the evaluation of liquid dosing processes can be obtained by repeatedly performing essentially the same liquid dosing process using essentially the same process parameter and thereby detecting the time characteristic of the at least one state variable. The phase "essentially the same process parameter" means that, if possible, the same liquid (or at least a liquid having essentially the same viscosity, surface tension, etc.) is dosed at essentially the same ambient temperature into essentially the same container, i.e., a container of the same design, e.g., the same order number from the same manufacturer, in essentially the same gas atmosphere with essentially the same operating settings of a dosing device. The operating settings of a dosing device include, for example, the dosing rate in volume of liquid per unit of time or weight of liquid per unit of time.

The scattering which occurs in practical use of a dosing device or the process parameters to be attributed to an exemplary scattering of the dosing device, e.g., measurement temperature, dosing rate and, as mentioned above, the shape of the container, shall thus be subsumed under "essentially the same" so that the setpoint range thus determined takes the scattering in parameters into account.

Assuming each individual dosing process has proceeded faultlessly, one obtains after repeatedly performing the liquid dosing process a set of time characteristics of the at least one state variable whose envelope curve can be used as the basis for additional performances of this liquid dosing process as the state variable setpoint range. Depending on the safety relevance of the quantity of liquid dosing or depending on the value of the liquid dosing, the envelope curve of most of the time characteristics of the at least one state variable may be increased or decreased by a tolerance amount, and the envelope curve thus increased or reduced may be used as the setpoint range.

As an alternative to that, the set of time characteristics of the at least one state variable may also be combined into a reference curve, e.g., by forming an average. This predetermined reference curve, provided with a bilateral tolerance field ($\pm n-6$), may also serve as a state variable setpoint range.

According to another preferred embodiment of the inventive method, a degree of correspondence of the time characteristic of the at least one state variable with the predetermined reference curve may be determined from the time characteristic of the at least one state variable by correlation calculation methods and an evaluation result pertaining to the dosing process may be output as a function of the result of the determination. By using correlation calculation methods, very precise comparisons of the time characteristic of the at least one state variable with the predetermined reference curve are possible. In addition, by performing a correlation calculation process and by storing a reference curve for certain operating parameters, it is possible to reduce the memory space required for storage of the state variable setpoint range and the computation time required for the comparison with a prevailing state variable characteristic may also be reduced. Therefore, the dosing process to be evaluated ca n also take place more rapidly. The calculated correlation coefficient may be used as a quality characteristic.

Known methods, e.g., fast Fourier transform, polynomial regression, regression methods in general, wavelets and differentiation, may be used as the correlation methods.

Such correlation calculation methods usually deliver the degree of correspondence between two curves or point curves as a numerical value. The dosing process to be investigated may then be evaluated as faulty, e.g., if the degree of correspondence determined is outside a predetermined degree of correspondence setpoint range. The evaluation result can be obtained particularly rapidly by this comparison of a numerical value with a predetermined value range, which is of great importance in view of the short time available in industrial dosing processes.

In addition, an error which occurs when the degree of correspondence is detected as being outside the predetermined degree of correspondence setpoint range can be investigated in greater detail by a more extensive diagnostic comparison method. In particular this determines whether the degree of correspondence is in an error range of a plurality of error ranges of a degree of correspondence value range which is outside the degree of correspondence setpoint range. Then an error message is output as a function of the error range in which the degree of correspondence is located. It is therefore possible to rapidly and reliably detect a systematic error in the dosing system and eliminate it. To do so, error ranges within the total degree of correspondence value range can be determined, e.g., in experiments and certain errors and/or error groups may be assigned to them, so that under some circumstances it is possible to make a statement regarding how critical the particular error is.

To be able to save on further computation time and further memory space, it is sufficient if the correlation calculation method uses as the input variable interpolation points from the time characteristic of the at least one variable state and from the reference curve. If there is a sufficiently small distance between the interpolation points, the computation time and the required memory space can be reduced considerably without any sacrifice of accuracy in the evaluation result.

According to another aspect of the invention, the object described above is also achieved by a device for evaluating a liquid dosing process in a container filled at least partially with gas, preferably air, using the method described above whereby the device comprises at least one sensor for detecting the time characteristic of the at least one state variable, a data memory for storing a predetermined state variable setpoint range of state variable values detected by the sensor and, if desired, points in time of detection of the individual state variable values, a data processing unit for comparison of the time characteristic of the least one state variable with the predetermined state variable setpoint range and an output unit for output of an evaluation result as a function of the result of the comparison by the data processing unit.

The at least one sensor is used to detect the time characteristic of the at least one state variable. This determination may be performed continuously or in individual measurements performed in time intervals, whereby the interval between two individual measurements is small in comparison with the total duration of the liquid dosing process.

The predetermined state variable setpoint range is stored in the data memory. In addition, the state variable values detected by the sensor are also stored in the data memory.

For example, a time characteristic may be formed from a plurality of individual measurements by assigning to each measurement a machine state or a container state which is characteristic of the dosing process, e.g., the position of a movable plunger relative to the remaining container. The position of the plunger is equivalent to a point in time at least during the phase in which the plunger is moving.

The device may also include a clock. If desired, as an alternative or in addition to the machine states mentioned above, the points in time assigned to a state variable determination may also be stored themselves. Storage of state variables together with the determination points in time assigned to them or machine states equivalent to them is necessary, e.g., when the determination of state variable values by at least one sensor is not performed at constant intervals. If state variable values are determined at constant intervals in time, however, then the storage of determination times may be omitted because the determination time can be determined from the sequence position of a state variable value in a series of state variable values.

In addition, this device also includes a data processing unit which uses data stored in the data memory for comparison of the time characteristic of the at least one state variable with the state variable setpoint range.

Finally, an output unit is used for output of an evaluation result which is obtained as a function of the result of the comparison by the data processing unit. The output unit may use alphanumeric characters and/or graphic elements, e.g., colored and/or structured lines and/or areas for output of the evaluation result and if desired for representing the time characteristic of the state variable as well as the state variable setpoint range.

In addition to the state variable setpoint range, a plurality of predetermined error ranges may also be stored in the data memory, each error range being assigned at least one possible error of the dosing process. In this way the data processing unit can diagnose the error(s) of the dosing process in question.

In addition, the device for creating the state variable setpoint range may include an editing unit with which a state variable setpoint range can be created, e.g., on the basis of a set of time characteristics.

The editing unit may include an input unit connected to it. Via this input unit it is possible to enter, for example, numerical values which define tolerance ranges by which an envelope curve of the set of time characteristics is widened or narrowed with respect to the set of curves.

As an alternative or in addition to that, the output unit of the device may be a graphic output unit, in which case then the input unit can also graphically determine a state variable setpoint range. This graphic method in which the set of time characteristics of the state variable and a state variable setpoint range, for example, are represented visually together is a particularly simple but nevertheless very effective option for creating a state variable setpoint range. However, with the editing unit a reference curve can be created graphically from the set of time characteristics. However, this may also be accomplished with greater accuracy by a computation process.

According to the preferred embodiments of the inventive method presented previously, the data processing unit may determine whether the time characteristic of the at least one state variable is within the predetermined state variable setpoint range. As an alternative or in addition to that, the data processing unit may also be designed to perform a correlation calculation process for determining a degree of correspondence of the time characteristic of the at least one state variable with a predetermined reference curve as the state variable setpoint range. It is advantageous here if a predetermined degree of correspondence setpoint range is stored in the data memory so that the degree of correspondence thus determined can be compared with it. In this way it is possible to determine whether the degree of correspondence thus determined is within the predetermined degree of correspondence setpoint range.

The above mentioned error ranges which may be stored in the data memory for error diagnosis may be, for example, degree of correspondence value ranges. Then a certain error and/or a certain error group is assigned to a certain range of degree of correspondence values.

It should be pointed out explicitly here that the two preferred embodiments mentioned above for increasing the evaluation reliability may also be used in combination for one and the same dosing process.

As already stated previously, the inventive method may be used to evaluate a liquid dosing process with any containers, any liquids and in any gas atmosphere. The same thing is also true of the device described above. However, this method is particularly suitable for pipetting processes, which is why the inventive device is preferably used on a pipetting system and/or the inventive method preferably evaluates a pipetting process on a pipetting system.

It is conceivable here that, in the case when a dosing that is evaluated as faulty, the method and/or the device may also order and/or perform measures in addition to merely performing an evaluation. This includes, for example, stopping a certain dosing process changing certain pipette tips, discarding a dosing process, e.g., aspiration and repeating this dosing process.

Figure 2:
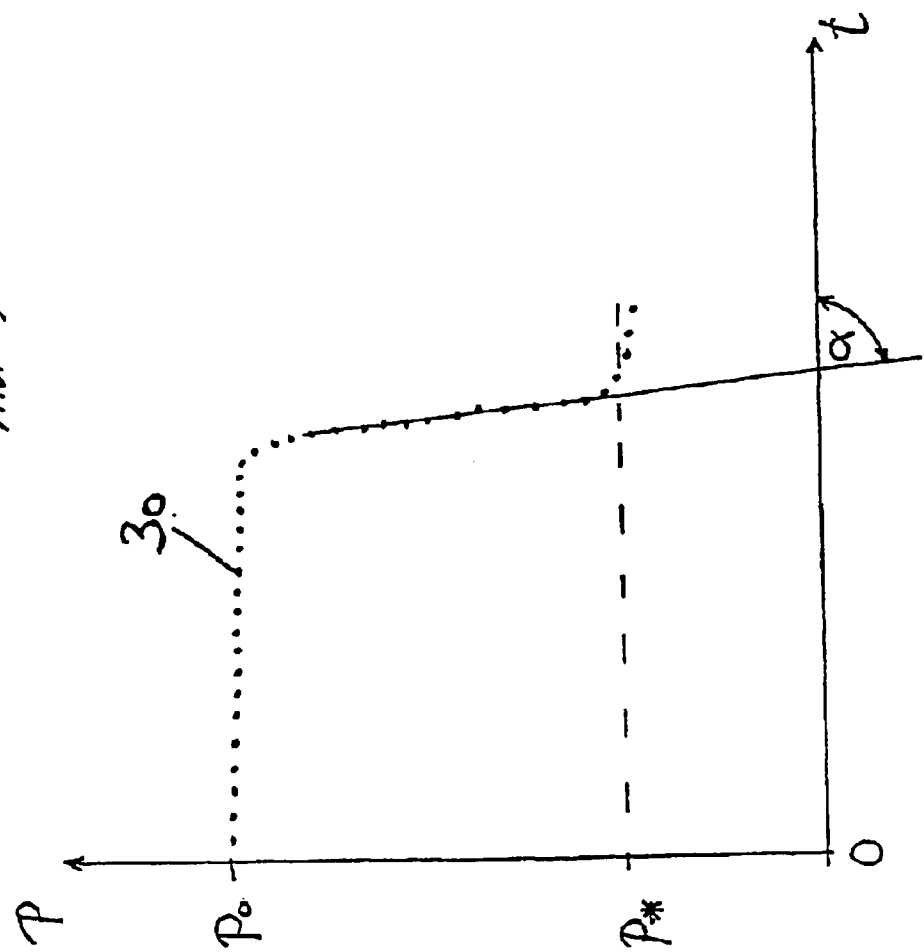
Figure 3:
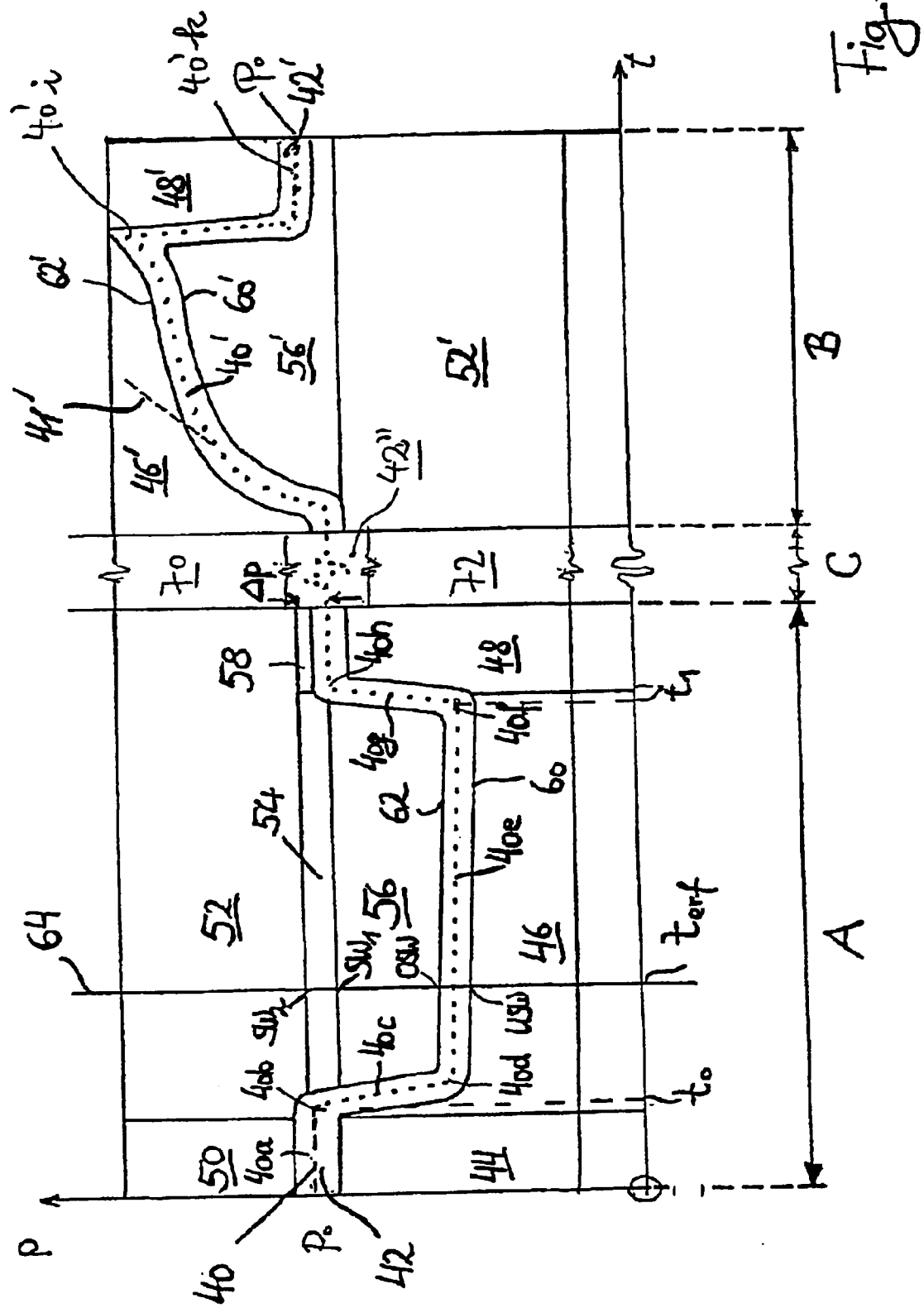
Figure 4:
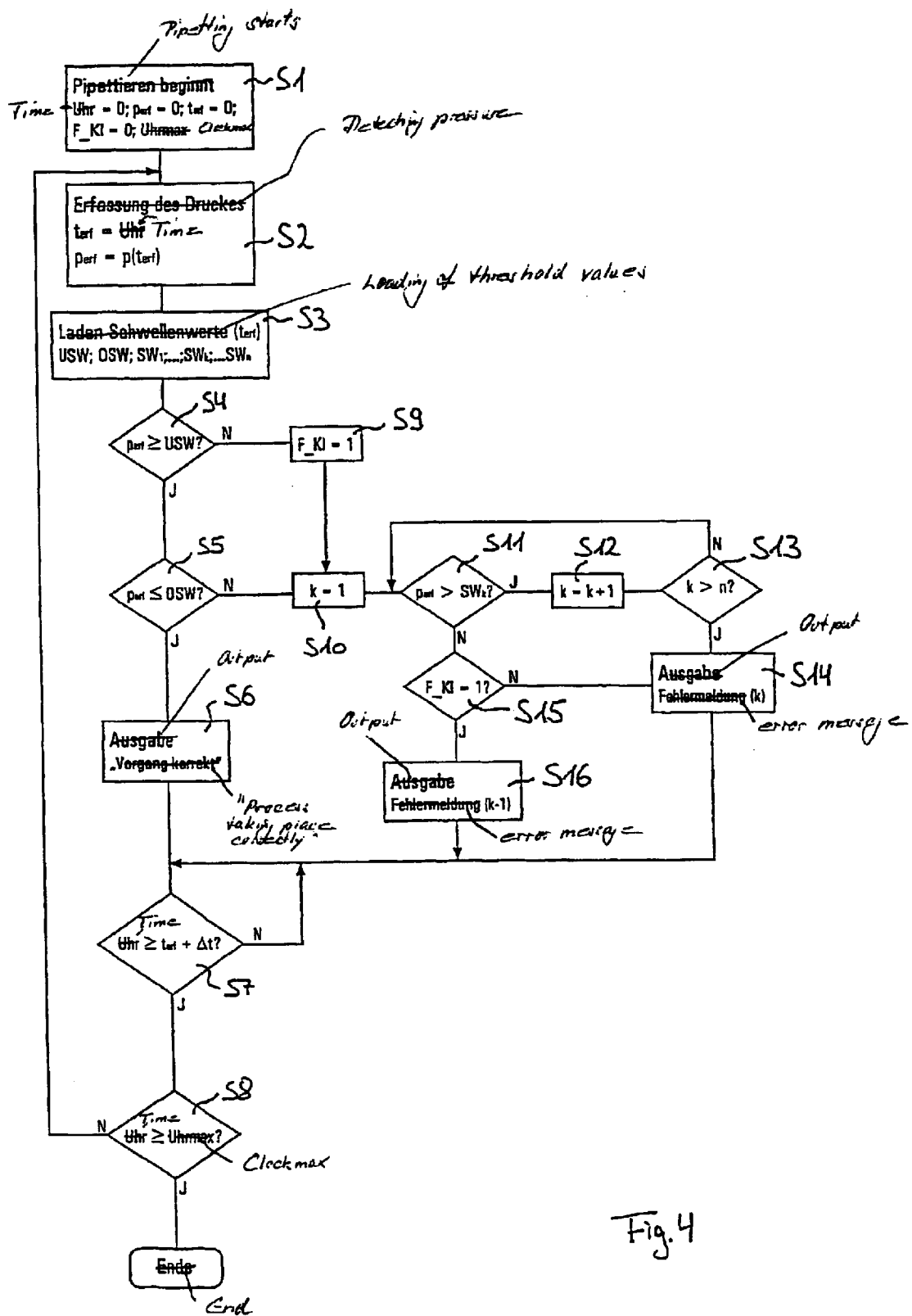

The present invention is explained in greater detail below on the basis of the accompanying drawings, which show:

FIGS. 1a–1e phases of an aspiration process in pipetting,

FIG. 2 a method of evaluating a liquid dosing process according to the state of the art, FIG. 3 a graphic representation of a time characteristic of the pressure of a gas present in the liquid holding space of a pipette tip in an aspiration and dispensing process, a state variable setpoint range according to the first preferred embodiment of this invention as well as error ranges surrounding the setpoint range, FIG. 4 a flow chart describing the first preferred embodiment of the inventive method, FIG. 5 a diagram showing the creation of state variable setpoint ranges of the preferred embodiments of the present invention.

On the basis of FIGS. 1a through 1e, a liquid aspiration process in pipetting on which the exemplary embodiment of the present invention is based will be explained briefly on the basis of schematic diagrams.

FIG. 1a shows a schematic cross section through a pipette tip 10 which moves toward the liquid level 14a of a liquid 14 in the direction of the arrow 12. A pressure detecting sensor 22 which detects the pressure of the gas present in the liquid holding space 20 is situated in the liquid holding space.

In FIG. 1b the opening 10a in the pipette tip 10 has reached the liquid level 14a. Therefore, the quantity of gas present in the liquid holding space 20 of the pipette tip 10 is separated from the ambient air and remains essentially constant apart from evaporation and condensation processes. The pipette tip 10 is also lowered in the direction of the arrow 12.

In FIG. 1c the pipette tip 10 has reached its lowest point and it remains with the opening 10a immersed in the liquid 14. The plunger 16 is now moved in the direction of the arrow 18, but no liquid has yet flowed into the liquid holding space 20 because of friction and surface tension effects.

It can be seen in FIG. 1d that the uptake of liquid 14 by the pipette tip 10 through the opening 10a has already begun. Then the plunger 16 is not moved any further (FIG. 1d'), so the volume of the liquid holding space 20 of the pipette tip 10 is not increased further. However, because of the negative pressure prevailing in the liquid holding space 20 with respect to the environment, liquid 14 continues to flow into the liquid holding space 20 until an equilibrium is established.

The aspiration process is concluded in FIG. 1e. The pipette tip 10 has been lifted out of the liquid 14. A certain volume of liquid 14 is in the liquid holding space 20 of the pipette tip 10 and is held there due to the negative pressure of the gas enclosed between the plunger 16 and the liquid volume with respect to the environment. In addition, friction and adhesion effects between the liquid volume and the wall of the pipette tip 10 also contribute to the liquid volume remaining in the pipette tip 10.

FIG. 2 shows a pressure-time diagram 30 of a state-of-the-art process for evaluating a liquid dosing process. The time t is plotted on the abscissa of the diagram in FIG. 2 and the pressure p of the quantity of gas present in the liquid holding space 20 is plotted on the ordinate.

The liquid dosing process is evaluated in such a way as to determine whether the pressure-time curve achieves a slope a in at least some segments, i.e., whether the rates of change in gas pressure reaches a predetermined value which is proportional to tan a in at least one segment and/or whether the pressure in the liquid holding space of the pipette tip falls below a predetermined limit value p* in aspiration. If the slope α is reached by the pressure-time curve in a period of time close to the start of aspiration and/or if it falls below the limit value p*, the aspiration process is evaluated as faulty. If one of the aforementioned conditions is not met, the aspiration process is evaluated as faulty.

In FIG. 3 the gas pressure in the liquid holding space 20 of the pipette tip 10 which is detected with the pressure detecting sensor 22 of FIGS. 1a through 1e during an aspiration process is represented by the dotted line 40 in time range A. This curve of pressure over time is plotted in a coordinate system. The time t is plotted on the abscissa and the pressure p of the gas in the liquid holding space 20 is plotted on the ordinate.

In addition, a pressure setpoint range 42 which follows a setpoint curve is also plotted in this coordinate system. In this diagram, the error ranges 44, 46 and 48, which are below the pressure setpoint range 42, as well as the error ranges 50, 52, 54, 56 and 58, which are above the pressure setpoint range 42, i.e., toward higher pressures, are outside the pressure setpoint range 42.

In FIG. 3, the time range A, the curve 40 of the gas pressure over time in the entire definition range of the pressure setpoint range 42 is within this range, which is why the dosing process in question is evaluated as faulty.

For a better understanding of the curve 40 of the gas pressure in the liquid holding space 20 of the pipette tip 10 of FIGS. 1a through 1e over time, the following brief explanation is given.

The curve begins at time t=0 at ambient pressure $p_0$. In the first segment 40a the pressure remains constant. This corresponds to the state shown in FIG. 1a where the volume of the liquid holding space 20 remains constant. As soon as the opening 10a in the pipette tip 10 as shown in FIG. 1b has reached the liquid level 14a, there is at first a slight reduction in pressure because of adhesion in the contact with the liquid surface which is then superimposed on the growing static pressure in the pipette tip as it is immersed to an increasing extent. Both effects are comparatively minor and therefore have not been entered into FIG. 3.

At a point in time which corresponds to FIG. 1c, the plunger 16 is moved upward in the direction of the arrow 18 at a constant rate, with the result that the pressure drops drastically. This phase of the drastic drop in pressure represented by segment 40c ends at point 40d, at which the liquid begins to flow into the liquid holding space 20 of the pipette tip. In the area 40e adjacent to the point 40d, any further increase in the gas volume of the quantity of gas enclosed in the liquid holding space 20 induced by the movement of the plunger 16 is diminished due to the liquid flowing into the liquid holding space 20, i.e., a liquid interface follows the plunger as it is raised. A dynamic equilibrium is established approximately between the increase in gas volume caused by the plunger and the reduction in volume caused by the inflowing liquid.

The movement of the plunger and thus the increase in volume of the liquid holding space end at time $t_1$ at point 40f (FIG. 1d). The negative pressure of the gas which is still present in the liquid holding space 20 with respect to the ambient gas of the pipette tip 10 allows more liquid to flow in the liquid holding space 20, so that the volume of the quantity of gas enclosed in the liquid holding space, a shown in segment 40g, is reduced rapidly and its pressure increases rapidly accordingly.

At point 40h, the pipette tip 10 has already been lifted up from the liquid (FIG. 1e). Shortly before this, the inflow of liquid into the liquid holding space 20 of the pipette tip 10 has ended (FIG. 1d'). At point 40h the quantity of gas enclosed between the plunger 16 and the liquid in the liquid holding space 20 is under a negative pressure difference p which is approximately proportional to the quantity of liquid dosed for sufficiently large dosed quantities of liquid. At very small quantities of liquid, i.e., at quantities less than approximately 30 μL, depending on the liquid, friction and adhesion effects between the liquid and the wall of the pipette tip are so strong that there is no direct proportionality between the negative pressure difference and the quantity of liquid dosed.

The individual error ranges 44, 46, 48, 50, 52, 54, 56 and 58 are delimited with respect to one another in time and by pressure values and/or pressure value curves over time. The pressure setpoint range 40 is delimited toward lower pressures by the lower threshold curve 60 and toward higher pressures by the upper threshold curve 62. The lower and upper threshold curves 60, 62 are functions of the pressure as a function of time and can be defined individually. For example, the following errors can be assigned to the different error ranges:

Error range 44: defective pressure measurement
Error range 46: pipette opening clogged
Error range 48: aspiration time too long
Error range 50: defective pressure measurement
Error range 52: aspiration and dispensation switched and pipette opening clogged
Error range 54: pipette tip leaky
Error range 56: aspiration process interrupted or air bubbles in the liquid
Error range 58: too little or no liquid in the pipette tip The curves of the gas pressure, the pressure setpoint range and error ranges surrounding the pressure setpoint range in the dispensing process are shown in time range B in FIG. 3. The dispensing process may take place, for example, following the aspiration process described previously or following a transport process in between (time range C). The same elements as in the time segment A of the aspiration process are provided with the same reference numbers with added primes in time segment B of the dispensing process. The error ranges in time segment B are numbered so that the ranges with a corresponding error assignment are designated with the same reference number plus a prime. The pressure at the time of the last liquid droplet is labeled as 40'$i$ and the equilibrium pressure which is established after the plunger comes to a standstill and which is derived from the ambient pressure $P_0$ is labeled as 40'$k$.

The following assignment of error messages and error ranges is applicable:
Error range 46': pipette opening clogged
Error range 48': dispensing time too long
Error range 52': aspiration and dispensation mixed up
Error range 56': pipette tip or pipetting system leaky Use of the error ranges is to be understood as follows. For example, if the pipetting opening is clogged in dispensation, the liquid present in the pipette tip cannot come out of the pipette tip or can do so only to a limited extent. Because of outward displacement movement of the plunger in dispensation, which reduces the volume of the liquid holding space of the pipette tip, the gas volume enclosed in the pipette tip is compressed. Therefore, the gas pressure increases. As a result the curve of the pressure over time leaves the setpoint range 42' and exceeds its upper threshold value 62', entering the error range 46'. This is indicated by the dotted line 41' in the time segment B in FIG. 3. In this way it is not only possible to reliably ascertain that an error has occurred during the liquid dosing process but also the error can be diagnosed.

In the time range in between, a pressure monitoring may also take place with an allowed pressure setpoint range 42" which is somewhat enlarged toward the top and bottom to take into account allowed pressure fluctuations in transport, in particular with a jerky movement.

If the pressure exceeds the setpoint range (error range 70) or if it falls below the setpoint range (error range 72), an error is detected.

FIG. 4 shows the course of an evaluation of a liquid dosing process in a flow chart. At step S1 the pipetting process begins, e.g., the aspiration process known from the time segment A in FIG. 3. At the beginning of the liquid dosing process, parameters that are relevant for the sequence are initialized, i.e., a clock is set at zero and started, the pressure $P_{erf}$ detected by a pressure detecting sensor at a detection point in time $t_{erf}$ is set at zero and likewise the detection point in time $t_{erf}$ [is set at zero]. In addition a flag F_KI which indicates in the error case whether the pressure has left the pressure setpoint range toward higher or lower pressure values is set at zero. The value $clock_{max}$ which indicates the duration of the liquid dosing process is loaded.

In the next step S2 the pressure of the gas present in the liquid holding space is detected and the momentary value of the clock is loaded into the variable $t_{erf}$ of the detection point in time. The pressure p measured at the detection point in time $t_{erf}$ is loaded into the variable $p_{erf}$, i.e., the pressure determination is performed at the point in time $t_{erf}$.

In the following step S3 the threshold values assigned to the respective detection point in time $t_{erf}$ are loaded from a memory. USW here denotes the lower threshold value of the pressure setpoint range (i.e., the value of the lower threshold curves 60 at the point in time $t_{erf}$ in FIG. 3) and OSW denotes the upper threshold value. $SW_1$ through $SW_n$ denote the threshold values which separate the individual error ranges. For example if the pressure determination is performed at the point in time $t_{erf}$ indicated by the line 64 in FIG. 3, then the point $SW_1$ is the threshold value separating the error range 56 from the error range 54 and the point $SW_2$ is the threshold value separating the error range 54 from the error range 52. The value n indicates the maximum number of threshold values between two error ranges. In the example shown in FIG. 3, n=2.

In the next step S4 a check is performed to determine whether the pressure $p_{erf}$ detected is equal to or greater than the lower threshold value USW which delimits the pressure setpoint range toward lower pressure values. If this is the case, then a check is performed in the next step S5 to determine whether the detected pressure $p_{erf}$ is smaller than or equal to the upper threshold value OSW which delimits the pressure setpoint range toward higher pressure values. If this is also the case, then in the next step S6 the information that the process is taking place correctly is output.

Step S7 representing a waiting loop which allows another pressure determination only when the period of time t has elapsed since the last pressure determination.

In step S8 a check is performed to determine whether or not the time limit $clock_{max}$ has been reached for the dosing process. If the time limit has been reached, the sequence ends, and if not, the sequence returns to step S2 and thus to a renewed determination of the gas pressure in the liquid holding space of the pipette tip.

If it is found in step S4 that the pressure $P_{erf}$ detected is lower than the lower threshold value USW, i.e., the curve of the gas pressure over time leaves the pressure setpoint range toward lower pressure values, then in a step S9 the flag F_KI is set at the value 1. In the following step S10 the running variable k=1 is set. If the curve of the pressure value over time leaves the pressure setpoint range toward higher pressure values, i.e., if it is found in step S5 that the pressure $p_{erf}$ detected is greater than the upper threshold value OSW, then step S10 is likewise reached but the flag F_KI remains at its initialization value of zero.

After it has already been determined that an error has occurred in the liquid dosing process, it is diagnosed in the steps described below. The following convention is used: at least one error message is assigned to each error range. The error messages are defined as a one-dimensional field (=vector), whereby the individual entries [for an] error message (x) in the error message field are assigned to the error ranges in the direction of increasing pressure, i.e., error message (0) is assigned to error range 46, error message (1) is assigned to error range 56, error message (2) is assigned to error range 54 and error message (3) is assigned to error range 52. Accordingly, the one-dimensional error message field contains a different number of entries as a function of the number of error ranges present at a certain point in time.

In step S11, the system determines whether the pressure $P_{erf}$ detected is greater than the $k^{th}$ threshold value. If this is the case, in step S12 the running variable k is incremented by one and a check is performed in step S13 to determine whether or not k has already exceeded the maximum number n of threshold values assigned to the point in time $t_{erf}$. If k has not yet exceeded this number, then the check of step S11 is repeated, but this time with a running variable that has been incremented by one.

However, if k exceeds the value n after being incremented by one, the pressure value tested must be in the error range having the highest pressure value range and in step S14, the error message (k) is output, i.e., in the present example this is error message (3) of error range 52.

If the check in step 11 reveals that the pressure $P_{erf}$ detected does not exceed the threshold $SW_k$, then in step S15 a check is performed is performed to determine whether the flag F_KI has a value of 1, i.e., whether the curve of the pressure overtime has broken out of the pressure setpoint range toward either higher or lower pressure values. If the flag F_KI has a value of zero, i.e., the pressure has left the pressure setpoint range toward higher pressure values, then the error message (k) is output. If the check in step S15, however, reveals that the value of the flag F_KI has a value of 1, i.e., the curve of pressure over time has left the pressure setpoint range in the direction of lower pressure values, then in step S16 the error message (k–1) is output. After output of the error message, the sequence in this example jumps to the waiting loop of step S7. However, it is also possible for the output of an error message to be followed by another procedure, e.g., an emergency off of a pipetting system or replacement of a pipette tip. However, it is also frequently interesting in the event of a faulty dosing process to monitor the course of the state variable detected over time until the end of the dosing process, because the time characteristic of the at least one state variable can under some circumstances reach several error ranges.

The device in which the inventive process takes place may be, for example, an electronic data processing system, in particular a personal computer or process-controlling microcontrollers. This data processing system is connected to at least one sensor at the tip of the pipette to detect the time characteristic of at least one state variable, e.g., the pressure. The data memory may be a hard drive, a CD-ROM, an internal RAM memory inside the computer system or a memory in a PC connected to the microcontroller. For example, the state variable setpoint range may be stored on a CD-ROM. The CPU of the data processing system forms the data processing unit, and a display screen or a printer constituted the output unit of the device. The CPU may also form an editing unit, in which case the data processing system will then include a keyboard or a mouse or the like as an input unit for editing of the state variable setpoint range.

The state variable measurement accompanying the dosing process may be analyzed, e.g., according to the flow chart described above, wherein a numerical departure of the instantaneous measured value from the tolerance range is detected. A graphic analysis (e.g., pattern recognition technology) is also conceivable for ascertaining whether, and if so, where the momentary measurement curve departs from the tolerance band.

Figure 5B:
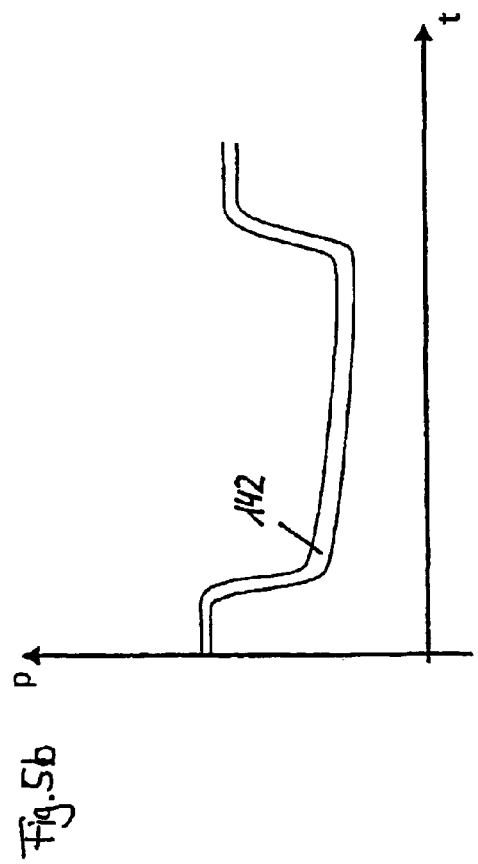
Figure 5C:
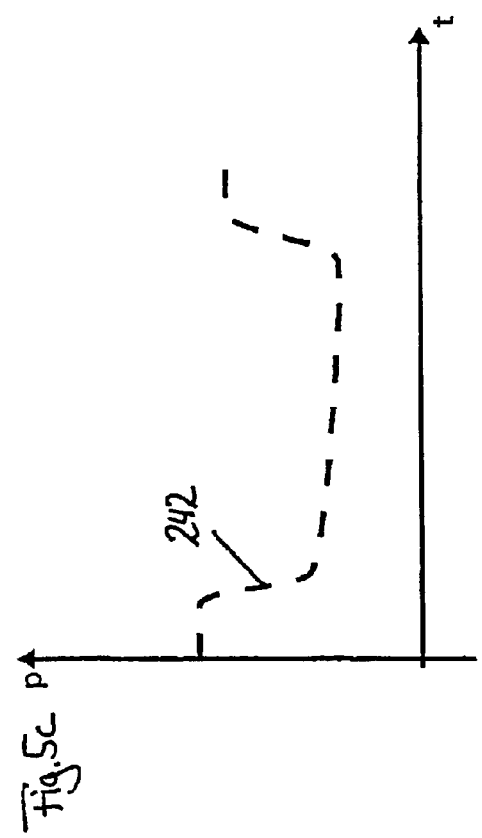
Figure 5A:
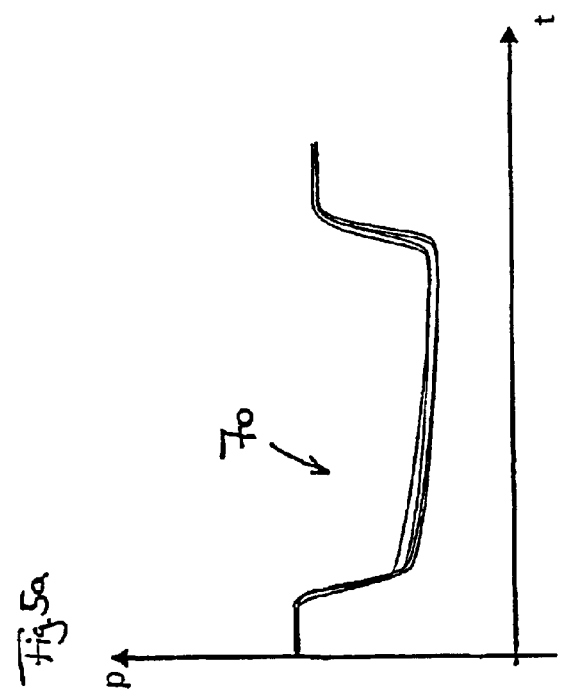

FIG. 5 shows the creation of state variable setpoint ranges for the preferred embodiments of this invention. FIG. 5a shows a pressure-time diagram (the time is plotted on the abscissa, pressure on the ordinate) in which a statistically significant set of curves 70 of pressure-time curves has been plotted; these curves were measured on a dosing process which was carried out with identical equipment and with identical working parameter settings. FIG. 5b shows a state variable setpoint range, i.e., pressure setpoint range 142 which is limited in the direction of higher and lower pressure values by the envelope curve of the set of curves 70 of FIG. 5a, for example. Accordingly, FIG. 5c shows a reference curve 242 which is obtained from the set of curves 70, e.g., by forming the average.

This reference curve 242 can be compared with a pressure-time curve measured currently, namely measured in a dosing process to be evaluated, by means of correlation calculation methods such as spectral analysis methods, preferably a fast Fourier transform and/or wavelets method and/or numeric convolution. The quality of the respective dosing process can be evaluated as a function of the degree of correspondence resulting from this correlation (*Numerical Mathematics*, H. R. Schwarz, Teubner Verlag Stuttgart; "Engineering Analysis" 1 and 2, Christian Blatter, Springer Verlag, 1996).

The degree of correspondence is usually a number which is standardized to have a value between 0 and 1, where 1 is the value for identical correspondence. A correspondence setpoint range extending from 0.9 to 1, for example, indicates the value range for whose degree of correspondence values a dosing process is evaluated as fault-free. In a value range from 0.4 to 0.9, for example, a questionable quality of the pipetting can be assumed, in which case a decision is to be made in the individual case as to whether or not to discard the pipetting. In the remaining value range (0 to 0.4 in this example), a serious mistake in pipetting is ascertained.

What is claimed is:

1. Method of evaluating a liquid dosing process in a pipette which is filed at least partially with a gas, preferably air, in particular an aspiration and/or dispensing process in pipetting, in which method a time characteristic (40; 40') of at least one state variable (p) of a medium present in the pipette is determined essentially over the entire duration of the dosing process; and in which it is determined whether the time characteristic (40; 40') of the at least one state variable (p) is within a predetermined state variable setpoint range (42; 42') which follows a setpoint curve, whereby an evaluation result (S6, S14, S16) is output as a function of the result of the determination, characterized in that the time characteristic of the at least one state variable (p) is determined during the change in the quantity of liquid in the pipette and is compared with an associated state variable setpoint range (42; 42'); wherein when the time characteristic (40; 40') of the at least one state variable (p) is outside of the state variable setpoint range (42; 42') in at least some segments, the method determines whether the time characteristic of the at least one state variable (p) lies in at least some segments in at least one error range of a plurality of error ranges (44, 46, 48, 50, 52, 54, 56, 58, 46', 48', 52', 56') of a state variable value range which is outside the state variable setpoint range (42; 42'), and an error message is output as a function of the at least one error range (46') which has been passed through.

2. Method according to claim 1, characterized in that the liquid dosing process is evaluated as faulty when it is determined that the time characteristic (40; 40') thus determined for the at least one state variable (p) is outside the state variable setpoint range (42; 42') in at least some segments.

3. Method according to claim 1, characterized in that the determination as to whether the time characteristic of the at least one state variable (p) is within the predetermined state variable setpoint range (42; 42') is performed by comparing the time characteristic (40; 40') with an upper threshold curve (62; 62') which delimits the state variable setpoint range (42; 42') toward larger state variable values and by comparison with a lower threshold curve (60; 60') which delimits the state variable setpoint range in the direction of smaller state variable values.

4. Method according to claim 1, characterized in that the determination as to whether the time characteristic (40; 40') of the at least one state variable (p) is within the predetermined state variable setpoint range (42; 42') is performed by image processing.

5. Method according to claim 1, characterized in that the medium is the gas present in the pipette.

6. Method according to claim 1, characterized in that the state variable is the pressure (p) and/or the temperature of the medium.

7. Method according to claim 1, characterized in that the state variable setpoint range (42; 42'; 242) is defined at least for the entire duration of the liquid dosing process, preferably also for the duration of a transport process in between.

8. Method according to claim 1, characterized in that the state variable setpoint range (42; 42'; 242) of a liquid dosing process is based on a plurality of performances (70) of essentially the same liquid dosing process using essentially the same process parameters.

9. Pipetting system in which a pipetting process is evaluated by a method according to claim 1.

10. Method of evaluating a liquid dosing process in a pipette, which is filled at least partially with a gas, preferably air, in particular an aspiration and/or dispensing process in pipetting, in which method a time characteristic (40, 40') of at least one state variable (p) of a medium present in the pipette is determined essentially over the entire duration of the dosing process; and essentially the entire time characteristic (40; 40') of the at least one gate variable (p) is compared with a predetermined state variable setpoint range (242) which follows a setpoint curve, characterized in that the time characteristic of the at least one state variable (p) is determined during the change in the quantity of liquid in the pipette and is compared with an associated state variable setpoint range (242), whereby a degree of correspondence of the time characteristic of the at least one state variable (p) with a predetermined reference curve as state variable setpoint range (242) is determined by means of correlation calculation methods, and an evaluation result is output as a function of the result of the determination; wherein when the degree of correspondence is determined as being outside the predetermined degree of correspondence setpoint range, determination is performed as to whether the degree of correspondence is in an error range of a plurality of error ranges of a degree of correspondence value range which is outside the correspondence setpoint range, and an error message is output as a function of the error range in which the degree of correspondence occurs.

11. Method according to claim 10, characterized in that the degree of correspondence as the result of the determination is a numerical value, whereby the liquid dosing process is evaluated as faulty if the degree of correspondence is outside a predetermined degree of correspondence setpoint range.

12. Method according to claim 10, characterized in that the correlation calculation method uses as input quantities interpolation points from the time characteristic of the at least one state variable (p) and from the reference curve.

13. Device for evaluating a liquid dosing process in a pipette which is filled at least partially with gas, preferably air, using the method according to claim 1, whereby the device comprises:

at least one sensor which is designed for detecting the time characteristic (40; 40') of at least one state variable (p) of a medium present in the pipette, preferably the gas, during the change in the quantity of liquid in the pipette, a data memory for storage of a predetermined state variable setpoint range (42; 42'; 242) which follows a setpoint curve and for storing state variable values (p) detected by the sensor, a data processing unit which is designed for comparing the time characteristic (40; 40') of the at least one state variable (p) with the predetermined state variable setpoint range (42; 42') during the change in the quantity of liquid in the pipette and for determining whether the time characteristic (40; 40') of the at least one state variable (p) is within the predetermined state variable setpoint range (42; 42'), and an output unit for output of an evaluation result (S6, S14, S16) as a function of the result of the comparison by the data processing unit.

14. Device according to claim 13, characterized in that a plurality of predetermined error ranges (44, 46, 48, 50, 52, 54, 56, 58; 46', 48', 52', 56') is stored in the data memory, at least one possible error of the dosing process being assigned to each error range (44, 46, 48, 50, 52, 54, 56, 58; 46', 48', 52', 56').

15. Pipetting system having an evaluation device according to claim 13.

16. Device according to claim 13, characterized in that the device also includes an editing unit for creating the state variable setpoint range.

17. Device according to claim 16, characterized in that the device includes an input unit connected to the editing unit.

18. Device according to claim 17, characterized in that the output unit is a graphic output unit, and a state variable setpoint range is graphically definable via the input unit.

19. Device for evaluating a liquid dosing process in a pipette, which is filled at least partially with gas, preferably air, using the method according to claim 10, whereby the device comprises:

at least one sensor which is designed for detecting the time characteristic (40; 40') of at least one state variable (p) of a medium present in the pipette, preferably the gas, during the change in the quantity of liquid in the pipette, a data memory for storage of a predetermined reference curve (242) as the state variable setpoint range (242) and for storing state variable values (p) detected by the sensor, a data processing unit which is designed for comparing the time characteristic (40; 40') of the at least one state variable (p) during the change in the quantity of liquid in the pipette with an associated state variable setpoint range (242), whereby the data processing unit is also designed to perform a correlation calculation method for determining a degree of correspondence of the time characteristic of the at least one state variable with the predetermined reference curve as the state variable setpoint range (242), an output unit for output of an evaluation result (S6, S14, S16) as a function of the result of the comparison by the data processing unit.

20. Device according to claim 19, characterized in that a predetermined degree of correspondence setpoint range is stored in the data memory.

21. Device according to claim 19, characterized in that the data processing unit determines whether the degree of correspondence is within the predetermined degree of correspondence setpoint range.

* * * * *